US012778801B2

(12) United States Patent
Govari

(10) Patent No.: US 12,778,801 B2
(45) Date of Patent: Nov. 3, 2026

(54) PRESSURE SENSING ARRAY IN PHACOEMULSIFICATION HANDPIECE

(71) Applicant: JOHNSON & JOHNSON SURGICAL VISION, INC., Irvine, CA (US)

(72) Inventor: Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 812 days.

(21) Appl. No.: 18/089,399

(22) Filed: Dec. 27, 2022

(65) Prior Publication Data

US 2024/0207092 A1 Jun. 27, 2024

(51) Int. Cl.
*A61M 1/00* (2006.01)
*A61F 9/007* (2006.01)

(52) U.S. Cl.
CPC ............... *A61F 9/007* (2013.01); *A61M 1/77* (2021.05); *A61M 2210/0612* (2013.01)

(58) Field of Classification Search
CPC ............ A61F 9/007; A61M 1/77; A61M 1/76
See application file for complete search history.

(56) References Cited

U.S. PATENT DOCUMENTS 2,094,830 A 10/1937 David
2,842,331 A 7/1958 Anderson
3,393,566 A 7/1968 Malcolm et al.
3,575,301 A 4/1971 Panissidi
3,920,014 A 11/1975 Banko
3,994,421 A 11/1976 Hansen
4,274,411 A 6/1981 Dotson, Jr.
4,291,706 A 9/1981 Voges et al.
4,384,578 A 5/1983 Winkler
4,555,940 A 12/1985 Renger
4,653,719 A 3/1987 Cabrera et al.
4,680,445 A 7/1987 Ogawa
(Continued)

FOREIGN PATENT DOCUMENTS

AU 2013202059 A1 4/2013
CN 108323001 A 7/2018
(Continued)

OTHER PUBLICATIONS

Cionni R.J., "Evaluating Two Key Safety Advances in the Centurion Vision System," ALCON, Cataract and Refractive Surgery Today, Aug. 2019, 4 pages.
(Continued)

*Primary Examiner* — Edelmira Bosques

(57) ABSTRACT

A phacoemulsification system includes a phacoemulsification probe and a processor. The phacoemulsification probe has a distal end configured for insertion into an eye of a patient, the probe including (i) an irrigation channel for irrigating the eye with irrigation fluid, (ii) an aspiration channel for evacuating material from the eye, and (iii) at least one sensor array fluidly coupled to at least one of the irrigation channel and the aspiration channel, the at least one sensor array comprising multiple sensors configured to measure a parameter indicative of fluid pressure in the irrigation channel or the aspiration channel. The processor is configured to regulate at least one of irrigation flow and aspiration flow using the measured parameter.

9 Claims, 5 Drawing Sheets

(56) References Cited

U.S. PATENT DOCUMENTS

| | | | |
|---|---|---|---|
| 4,702,733 | A | 10/1987 | Wright et al. |
| 4,818,186 | A | 4/1989 | Pastrone et al. |
| 4,832,685 | A | 5/1989 | Haines |
| 4,902,034 | A | 2/1990 | Maguran et al. |
| 4,935,005 | A | 6/1990 | Haines |
| 4,954,960 | A | 9/1990 | Lo et al. |
| 5,032,111 | A | 7/1991 | Morris et al. |
| 5,047,009 | A | 9/1991 | Morris et al. |
| 5,106,367 | A | 4/1992 | Ureche et al. |
| 5,108,372 | A | 4/1992 | Swenson |
| 5,135,485 | A | 8/1992 | Cohen et al. |
| 5,167,620 | A | 12/1992 | Ureche et al. |
| 5,190,042 | A | 3/1993 | Hock |
| 5,242,404 | A | 9/1993 | Conley et al. |
| 5,328,456 | A | 7/1994 | Horiguchi et al. |
| 5,354,268 | A | 10/1994 | Peterson et al. |
| 5,405,269 | A | 4/1995 | Stupecky |
| 5,417,246 | A | 5/1995 | Perkins et al. |
| 5,429,601 | A | 7/1995 | Conley et al. |
| 5,476,448 | A | 12/1995 | Urich |
| 5,487,827 | A | 1/1996 | Peterson et al. |
| 5,569,188 | A | 10/1996 | Mackool |
| 5,591,127 | A | 1/1997 | Barwick, Jr. et al. |
| 5,616,120 | A | 4/1997 | Andrew et al. |
| 5,649,905 | A | 7/1997 | Zanger et al. |
| 5,693,013 | A | 12/1997 | Geuder |
| 5,695,473 | A | 12/1997 | Olsen |
| 5,697,898 | A | 12/1997 | Devine |
| 5,700,240 | A | 12/1997 | Barwick, Jr. et al. |
| 5,733,256 | A | 3/1998 | Costin |
| 5,766,146 | A | 6/1998 | Barwick, Jr. |
| 5,810,765 | A | 9/1998 | Oda |
| 5,827,223 | A | 10/1998 | Butterfield |
| 5,865,764 | A | 2/1999 | Moorhead |
| 5,885,243 | A | 3/1999 | Capetan et al. |
| 5,910,110 | A | 6/1999 | Bastable |
| 5,921,554 | A | 7/1999 | Derian et al. |
| 5,935,106 | A | 8/1999 | Olsen |
| 6,050,496 | A | 4/2000 | Hefler |
| 6,083,193 | A | 7/2000 | Kadziauskas et al. |
| 6,159,175 | A | 12/2000 | Strukel et al. |
| 6,167,588 | B1 | 1/2001 | Dyson |
| 6,170,383 | B1 | 1/2001 | Mauritz |
| 6,179,808 | B1 | 1/2001 | Boukhny et al. |
| 6,190,354 | B1 | 2/2001 | Sell et al. |
| 6,383,203 | B1 | 5/2002 | Makihara |
| 6,423,029 | B1 | 7/2002 | Elsberry |
| 6,491,661 | B1 | 12/2002 | Boukhny et al. |
| 6,533,747 | B1 | 3/2003 | Polaschegg et al. |
| 6,565,535 | B2 | 5/2003 | Zaias et al. |
| 6,579,255 | B2 | 6/2003 | Kadziauskas et al. |
| 6,599,271 | B1 | 7/2003 | Easley |
| 6,648,223 | B2 | 11/2003 | Boukhny et al. |
| 6,681,730 | B1 | 1/2004 | Koneda et al. |
| 6,740,058 | B2 | 5/2004 | Lal et al. |
| 6,780,166 | B2 | 8/2004 | Kanda et al. |
| 6,986,753 | B2 | 1/2006 | Bui |
| 7,083,591 | B2 | 8/2006 | Cionni |
| 7,146,864 | B2 | 12/2006 | Sullivan et al. |
| 7,297,137 | B2 | 11/2007 | Gordon et al. |
| 7,670,330 | B2 | 3/2010 | Claus et al. |
| 7,695,447 | B2 | 4/2010 | Khashayar et al. |
| 7,785,336 | B2 | 8/2010 | Staggs |
| 7,811,255 | B2 | 10/2010 | Boukhny et al. |
| 8,246,580 | B2 | 8/2012 | Hopkins et al. |
| 8,380,126 | B1 | 2/2013 | Ma et al. |
| 8,425,452 | B2 | 4/2013 | Claus et al. |
| 8,430,840 | B2 | 4/2013 | Nazarifar et al. |
| 8,430,841 | B2 | 4/2013 | Claus et al. |
| 8,444,592 | B2 | 5/2013 | Williams et al. |
| 8,479,585 | B2 | 7/2013 | Shaw-Klein |
| 8,491,528 | B2 | 7/2013 | Muri et al. |
| 8,523,812 | B2 | 9/2013 | Boukhny et al. |
| 8,617,106 | B2 | 12/2013 | Zacharias |
| 8,652,086 | B2 | 2/2014 | Gerg et al. |
| 8,668,665 | B2 | 3/2014 | Gerg et al. |
| 8,715,220 | B2 | 5/2014 | Gerg et al. |
| 8,721,594 | B2 | 5/2014 | Zacharias |
| 9,198,798 | B2 | 12/2015 | Claus et al. |
| 9,482,563 | B2 | 11/2016 | Calderin et al. |
| 9,549,851 | B2 | 1/2017 | Chon et al. |
| 9,610,193 | B2 | 4/2017 | Velasco et al. |
| 9,610,913 | B2 | 4/2017 | Narita |
| 9,782,232 | B1 | 10/2017 | Papac |
| 9,795,507 | B2 | 10/2017 | Hajishah et al. |
| 9,861,522 | B2 | 1/2018 | Sorensen et al. |
| 9,931,447 | B2 | 4/2018 | Layser et al. |
| 10,125,877 | B2 | 11/2018 | Morgan et al. |
| 10,182,940 | B2 | 1/2019 | Chandrakant et al. |
| 10,278,861 | B2 | 5/2019 | Bourne |
| 10,463,780 | B2 | 11/2019 | Mallough et al. |
| 10,470,926 | B2 | 11/2019 | Zacharias |
| 10,500,319 | B2 | 12/2019 | Banko |
| 10,518,005 | B2 | 12/2019 | Carr et al. |
| 10,702,415 | B2 | 7/2020 | Charles |
| 11,033,897 | B2 | 6/2021 | Szita et al. |
| 11,051,978 | B2 | 7/2021 | Heeren et al. |
| 11,071,816 | B2 | 7/2021 | Mehta et al. |
| 11,185,623 | B2 | 11/2021 | Ovchinnikov et al. |
| 11,383,020 | B2 | 7/2022 | Keh et al. |
| 11,446,424 | B2 | 9/2022 | Mehta et al. |
| 11,602,586 | B2 | 3/2023 | Bourne et al. |
| 2001/0023331 | A1 | 9/2001 | Kanda et al. |
| 2002/0019607 | A1 | 2/2002 | Bui |
| 2002/0174910 | A1 | 11/2002 | Willeke, Jr. et al. |
| 2002/0193817 | A1 | 12/2002 | Lal et al. |
| 2003/0006729 | A1 | 1/2003 | Raymond |
| 2003/0050613 | A1 | 3/2003 | Hammerslag |
| 2003/0050619 | A1 | 3/2003 | Mooijman et al. |
| 2003/0078487 | A1 | 4/2003 | Jeffries et al. |
| 2003/0105437 | A1 | 6/2003 | Neubert |
| 2004/0092885 | A1 | 5/2004 | Duchon et al. |
| 2004/0092921 | A1 | 5/2004 | Kadziauskas et al. |
| 2004/0101445 | A1 | 5/2004 | Shvets et al. |
| 2005/0054971 | A1 | 3/2005 | Steen et al. |
| 2005/0080375 | A1 | 4/2005 | Kadziauskas et al. |
| 2005/0096593 | A1 | 5/2005 | Pope et al. |
| 2005/0118048 | A1 | 6/2005 | Traxinger |
| 2005/0181018 | A1 | 8/2005 | Peyman |
| 2005/0209560 | A1 | 9/2005 | Boukhny et al. |
| 2005/0209621 | A1 | 9/2005 | Gordon et al. |
| 2005/0228423 | A1 | 10/2005 | Khashayar et al. |
| 2005/0234441 | A1 | 10/2005 | Bisch et al. |
| 2005/0261628 | A1 | 11/2005 | Boukhny et al. |
| 2005/0261715 | A1 | 11/2005 | Boukhny et al. |
| 2005/0267504 | A1 | 12/2005 | Boukhny et al. |
| 2006/0058811 | A1 | 3/2006 | Kishimoto et al. |
| 2006/0064053 | A1 | 3/2006 | Bollish et al. |
| 2006/0224107 | A1 | 10/2006 | Claus et al. |
| 2006/0224143 | A1 | 10/2006 | Claus et al. |
| 2006/0224163 | A1 | 10/2006 | Sutton |
| 2006/0281986 | A1 | 12/2006 | Orilla et al. |
| 2007/0005029 | A1 | 1/2007 | Hopkins et al. |
| 2007/0227265 | A1 | 10/2007 | Sugi et al. |
| 2007/0270744 | A1 | 11/2007 | Dacquay et al. |
| 2008/0000485 | A1 | 1/2008 | Williams et al. |
| 2008/0015406 | A1 | 1/2008 | Dlugos et al. |
| 2008/0033349 | A1 | 2/2008 | Suzuki |
| 2008/0053560 | A1 | 3/2008 | Hartman et al. |
| 2008/0112828 | A1 | 5/2008 | Muri et al. |
| 2008/0114289 | A1 | 5/2008 | Muri et al. |
| 2008/0114290 | A1 | 5/2008 | King et al. |
| 2008/0125698 | A1 | 5/2008 | Gerg et al. |
| 2008/0154095 | A1 | 6/2008 | Stubkjaer et al. |
| 2008/0177126 | A1 | 7/2008 | Tate et al. |
| 2008/0319374 | A1 | 12/2008 | Zacharias |
| 2008/0319451 | A1 | 12/2008 | Zacharias |
| 2009/0013780 | A1 | 1/2009 | Gao et al. |
| 2009/0048607 | A1 | 2/2009 | Rockley |
| 2009/0128160 | A1* | 5/2009 | Chiaburu ................. G01D 3/08 702/58 |
| 2009/0158855 | A1 | 6/2009 | Holden |
| 2009/0163863 | A1 | 6/2009 | Lutwyche |
| 2009/0302671 | A1 | 12/2009 | Brooks |

(56) References Cited

U.S. PATENT DOCUMENTS

| | | | |
|---|---|---|---|
| 2010/0030134 | A1 | 2/2010 | Fitzgerald et al. |
| 2010/0111735 | A1 | 5/2010 | Tu |
| 2010/0121257 | A1 | 5/2010 | King |
| 2010/0125246 | A1 | 5/2010 | Kalpin |
| 2010/0130915 | A1 | 5/2010 | Claus et al. |
| 2010/0145302 | A1 | 6/2010 | Cull et al. |
| 2010/0174238 | A1 | 7/2010 | Sher |
| 2010/0185150 | A1 | 7/2010 | Zacharias |
| 2010/0249693 | A1 | 9/2010 | Links |
| 2010/0280435 | A1 | 11/2010 | Raney et al. |
| 2010/0292631 | A1 | 11/2010 | Holden et al. |
| 2010/0312170 | A1 | 12/2010 | Maaskamp et al. |
| 2011/0027118 | A1 | 2/2011 | Milovanovic |
| 2011/0066122 | A1* | 3/2011 | Stanton ............ A61B 17/32002 604/319 |
| 2011/0087156 | A1 | 4/2011 | Claus |
| 2011/0092891 | A1 | 4/2011 | Gerg et al. |
| 2011/0092896 | A1 | 4/2011 | Kuebler et al. |
| 2011/0112472 | A1 | 5/2011 | Jacobson et al. |
| 2011/0152728 | A1 | 6/2011 | Teodorescu |
| 2011/0257591 | A1 | 10/2011 | Nelson Konen et al. |
| 2011/0284777 | A1 | 11/2011 | Pitchford et al. |
| 2011/0295191 | A1 | 12/2011 | Injev |
| 2011/0313343 | A1 | 12/2011 | Milutinovic et al. |
| 2012/0004595 | A1 | 1/2012 | DuBois et al. |
| 2012/0041362 | A1 | 2/2012 | Gerg et al. |
| 2012/0265144 | A1 | 10/2012 | Kalpin et al. |
| 2013/0060210 | A1 | 3/2013 | Ross et al. |
| 2013/0060211 | A1 | 3/2013 | Adams, Jr. |
| 2013/0062543 | A1 | 3/2013 | Shiao et al. |
| 2013/0123680 | A1 | 5/2013 | Ha et al. |
| 2013/0131578 | A1 | 5/2013 | Stalmans et al. |
| 2013/0150782 | A1 | 6/2013 | Sorensen et al. |
| 2013/0197471 | A1 | 8/2013 | Williams et al. |
| 2013/0246079 | A1 | 9/2013 | Hoffman et al. |
| 2014/0100518 | A1 | 4/2014 | Baxter et al. |
| 2014/0107459 | A1 | 4/2014 | Lind et al. |
| 2014/0114236 | A1 | 4/2014 | Gordon et al. |
| 2014/0114237 | A1 | 4/2014 | Gordon |
| 2014/0163455 | A1* | 6/2014 | Wilson ................. A61M 1/774 604/28 |
| 2014/0171869 | A1 | 6/2014 | Zhang |
| 2014/0206940 | A1 | 7/2014 | Hufford |
| 2014/0257172 | A1* | 9/2014 | Yalamanchili ...... A61M 3/0283 604/22 |
| 2014/0282018 | A1 | 9/2014 | Amble et al. |
| 2014/0323953 | A1 | 10/2014 | Sorensen et al. |
| 2014/0364799 | A1 | 12/2014 | Beauvais et al. |
| 2015/0057524 | A1 | 2/2015 | Artsyukhovich et al. |
| 2015/0157501 | A1 | 6/2015 | Bourne et al. |
| 2015/0173629 | A1* | 6/2015 | Corl .................. A61B 5/02158 600/486 |
| 2015/0359666 | A1 | 12/2015 | Zacharias |
| 2016/0128869 | A1 | 5/2016 | Zacharias |
| 2016/0175578 | A1 | 6/2016 | Roholt |
| 2016/0220751 | A1 | 8/2016 | Mallough et al. |
| 2016/0228061 | A1 | 8/2016 | Källbäck et al. |
| 2016/0346123 | A1 | 12/2016 | Koplin |
| 2016/0367735 | A1 | 12/2016 | Eddo et al. |
| 2017/0022488 | A1 | 1/2017 | Bermudez et al. |
| 2017/0224888 | A1 | 8/2017 | Hickey et al. |
| 2017/0246419 | A1 | 8/2017 | Callaghan et al. |
| 2017/0312431 | A1 | 11/2017 | Johnson et al. |
| 2017/0326000 | A1 | 11/2017 | Heeren et al. |
| 2017/0333253 | A1 | 11/2017 | Heeren et al. |
| 2017/0367885 | A1 | 12/2017 | Bourne |
| 2017/0367887 | A1 | 12/2017 | Muri et al. |
| 2018/0028359 | A1 | 2/2018 | Gordon et al. |
| 2018/0049220 | A1 | 2/2018 | Patil et al. |
| 2018/0049920 | A1 | 2/2018 | Charles |
| 2018/0078415 | A1 | 3/2018 | Citterio et al. |
| 2018/0092774 | A1 | 4/2018 | Mehta et al. |
| 2018/0279876 | A1 | 10/2018 | Paschalis |
| 2018/0296738 | A1 | 10/2018 | King et al. |
| 2018/0304012 | A1 | 10/2018 | Jansen |
| 2018/0318131 | A1 | 11/2018 | Boukhny et al. |
| 2018/0338861 | A1 | 11/2018 | Hallen |
| 2019/0099526 | A1 | 4/2019 | Hajishah et al. |
| 2019/0099529 | A1 | 4/2019 | Mehta et al. |
| 2019/0099546 | A1 | 4/2019 | Keh et al. |
| 2019/0099547 | A1 | 4/2019 | Mehta et al. |
| 2019/0099548 | A1 | 4/2019 | Mehta et al. |
| 2019/0133822 | A1 | 5/2019 | Banko |
| 2019/0143008 | A1 | 5/2019 | Brundage et al. |
| 2019/0176557 | A1 | 6/2019 | Marking et al. |
| 2019/0200885 | A1 | 7/2019 | Jacobsen |
| 2019/0262175 | A1 | 8/2019 | Kerkhoff et al. |
| 2019/0282401 | A1 | 9/2019 | Sorensen et al. |
| 2019/0365567 | A1 | 12/2019 | Balkenbush et al. |
| 2020/0030147 | A1 | 1/2020 | Koplin |
| 2020/0107958 | A1 | 4/2020 | Wong et al. |
| 2020/0337900 | A1 | 10/2020 | Nazarifar et al. |
| 2020/0360594 | A1 | 11/2020 | Dam-huisman |
| 2021/0106734 | A1 | 4/2021 | Mehta et al. |
| 2021/0153741 | A1 | 5/2021 | Berdahl et al. |
| 2021/0353145 | A1 | 11/2021 | Kamthan et al. |
| 2021/0386927 | A1 | 12/2021 | Mehta et al. |
| 2021/0386928 | A1 | 12/2021 | Mehta et al. |
| 2022/0133537 | A1 | 5/2022 | Govari et al. |
| 2022/0192876 | A1 | 6/2022 | Algawi et al. |
| 2022/0192877 | A1 | 6/2022 | Algawi et al. |
| 2022/0193322 | A1 | 6/2022 | Govari et al. |
| 2023/0190525 | A1 | 6/2023 | Yan et al. |
| 2023/0390478 | A1 | 12/2023 | Fung et al. |
| 2024/0108503 | A1 | 4/2024 | Gliner et al. |
| 2024/0115421 | A1 | 4/2024 | Govari et al. |

FOREIGN PATENT DOCUMENTS

| | | | |
|---|---|---|---|
| CN | 110338970 | A | 10/2019 |
| CN | 108323001 | B | 4/2020 |
| CN | 116250982 | A | 6/2023 |
| DE | 19753636 | A1 | 9/1999 |
| DE | 20318275 | U1 | 2/2004 |
| EP | 0997363 | A2 | 5/2000 |
| EP | 1382291 | A2 | 1/2004 |
| EP | 1471342 | A2 | 10/2004 |
| EP | 1900347 | A1 | 3/2008 |
| EP | 1471342 | B1 | 8/2009 |
| EP | 2320842 | A2 | 5/2011 |
| EP | 2379126 | A2 | 10/2011 |
| EP | 2320842 | B1 | 6/2012 |
| EP | 2164435 | B1 | 8/2012 |
| EP | 2919850 | B1 | 10/2018 |
| JP | S62500640 | A | 3/1987 |
| JP | 2001161740 | A | 6/2001 |
| JP | 2003225247 | A | 8/2003 |
| RU | 2720821 | C1 | 5/2020 |
| WO | 8906522 | A2 | 7/1989 |
| WO | 9945868 | A1 | 9/1999 |
| WO | 0194893 | A1 | 12/2001 |
| WO | 03047653 | A1 | 6/2003 |
| WO | 2004108189 | A2 | 12/2004 |
| WO | 2004110524 | A2 | 12/2004 |
| WO | 2005037156 | A1 | 4/2005 |
| WO | 2007143797 | A1 | 12/2007 |
| WO | 2008030872 | A1 | 3/2008 |
| WO | 2008157674 | A1 | 12/2008 |
| WO | 2009076717 | A1 | 6/2009 |
| WO | 2009076717 | A9 | 8/2009 |
| WO | 2010124755 | A1 | 11/2010 |
| WO | 2011045033 | A1 | 4/2011 |
| WO | 2011105909 | A1 | 9/2011 |
| WO | 2014151209 | A1 | 9/2014 |
| WO | 2016122790 | A1 | 8/2016 |
| WO | 2016148754 | A1 | 9/2016 |
| WO | 2016150754 | A1 | 9/2016 |
| WO | 2016191665 | A1 | 12/2016 |
| WO | 2017044138 | A1 | 3/2017 |
| WO | 2018033877 | A1 | 2/2018 |
| WO | 2018064625 | A1 | 4/2018 |
| WO | 2019068151 | A1 | 4/2019 |
| WO | 2019115584 | A1 | 6/2019 |
| WO | 2021083938 | A1 | 5/2021 |

(56) References Cited

FOREIGN PATENT DOCUMENTS

OTHER PUBLICATIONS

Gopesh T., et al., "Rapid and Accurate Pressure Sensing Device for Direct Measurement of Intraocular Pressure," Translational Vision Science and Technology (TVST), Feb. 2020, vol. 9 (3), Article 28, pp. 1-9.
Miller K.M., et al., "Millennialeye," Supplement to Contract Refractive Surgery Today, Sep./Oct. 2019, 16 pages.
Bello et al., "Development of a Smart Pump for Monitoring and Controlling Intraocular Pressure", Annals of Biomedical Engineering, vol. 45, No. 4, pp. 990-1002, Apr. 2017.
U.S. Appl. No. 17/130,409, filed Dec. 22, 2020, and titled, "A module for Aspiration and Irrigation Control".
Yao, Jia-lin & Yang, Xing & Shao, Na & Luo, Hui & Zhang, Ting & Jiang, Wu-gui. (2016). A Flexible and Highly Sensitive Piezoresistive Pressure Sensor Based on Micropatterned Films Coated with Carbon Nanotubes. Journal of Nanomaterials. 2016. 1-5. 10.1155/2016/3024815.
International Preliminary Report on Patentability received for PCT Application No. PCT/US2007/066248, mailed on Oct. 14, 2008, 6 pages.
Thomas et al., "Phaco Machine basics", Pearls in Ophthalmology, 5 pages, Jul. 17, 2010.

* cited by examiner

PRESSURE SENSING ARRAY IN PHACOEMULSIFICATION HANDPIECE

FIELD OF THE DISCLOSURE

The present disclosure relates generally to phacoemulsification systems and probes, and particularly to measurement of aspiration and irrigation parameters.

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

The present disclosure will be more fully understood from the following detailed description of the examples thereof, taken together with the drawings in which:

DETAILED DESCRIPTION OF EXAMPLES

Overview

A phacoemulsification procedure for cataract removal requires strict control over intraocular pressure (IOP) to prevent damage to the eye. Real-time control over IOP can be made more robust if aspiration and irrigation parameter readings, such as of irrigation fluid pressure, aspiration vacuum level and aspiration and/or irrigation flow rates are acquired from sensors embedded at a distal end of the phacoemulsification handpiece.

Phacoemulsification handpiece typically includes dedicated rigid channels through which irrigation and aspiration is directed. One possible way to achieve robust real-time control over IOP is to embed a vacuum sensor in the aspiration channel of the handpiece and a pressure sensor in the irrigation channel of the handpiece. The sensors may be fluidly coupled to respective aspiration and irrigation channels located inside a handpiece of the phacoemulsification device (e.g., probe). In this way, the sensors measure the aspiration and/or irrigation through the handpiece no more than a few centimeters or tens of centimeters away from the eye itself.

However, as the handpiece is a reusable part, it undergoes sterilization between uses that frequently subjects the sensor to a harsh environment (such as large temperature variations and degradation of seals by steam). Moreover, a handpiece may fall or experience other mechanical damage that subjects the sensors to mechanical shock. As a result of all these stresses, the aforementioned pressure/vacuum sensors may malfunction without the user's knowledge. Operating a handpiece with a faulty pressure sensor or vacuum sensor may be hazardous to the patient.

During priming, a user covers the phacoemulsification tip with a flexible cover and then let fluid run through both the aspiration and the irrigation line to take out all the air from the system. Testing the sensors before each procedure may indicates malfunction of individual sensors. Yet, readings from a single sensor reading may be misleading (e.g., in the absence of a reference).

Examples of the present disclosure that are described hereinafter verify the integrity of the pressure/vacuum sensors during the priming phase run before each surgical procedure (e.g., phacoemulsification procedure). To this end, the disclosed technique provides sensor arrays that are embedded into a handpiece of a phacoemulsification probe. The system measures pressure with the multiple sensors and compares the readings. If readings from all sensors provide same output this is an indication that the pressure sensors are operating correctly. If not, then apparently there has been some damage and the handpiece is faulty. During the surgical procedure, the system optionally continues to measure pressure from all sensors to make sure that similar readings are received from the sensors on each of the rigid channels. The system may use the average readings.

Figure 4:
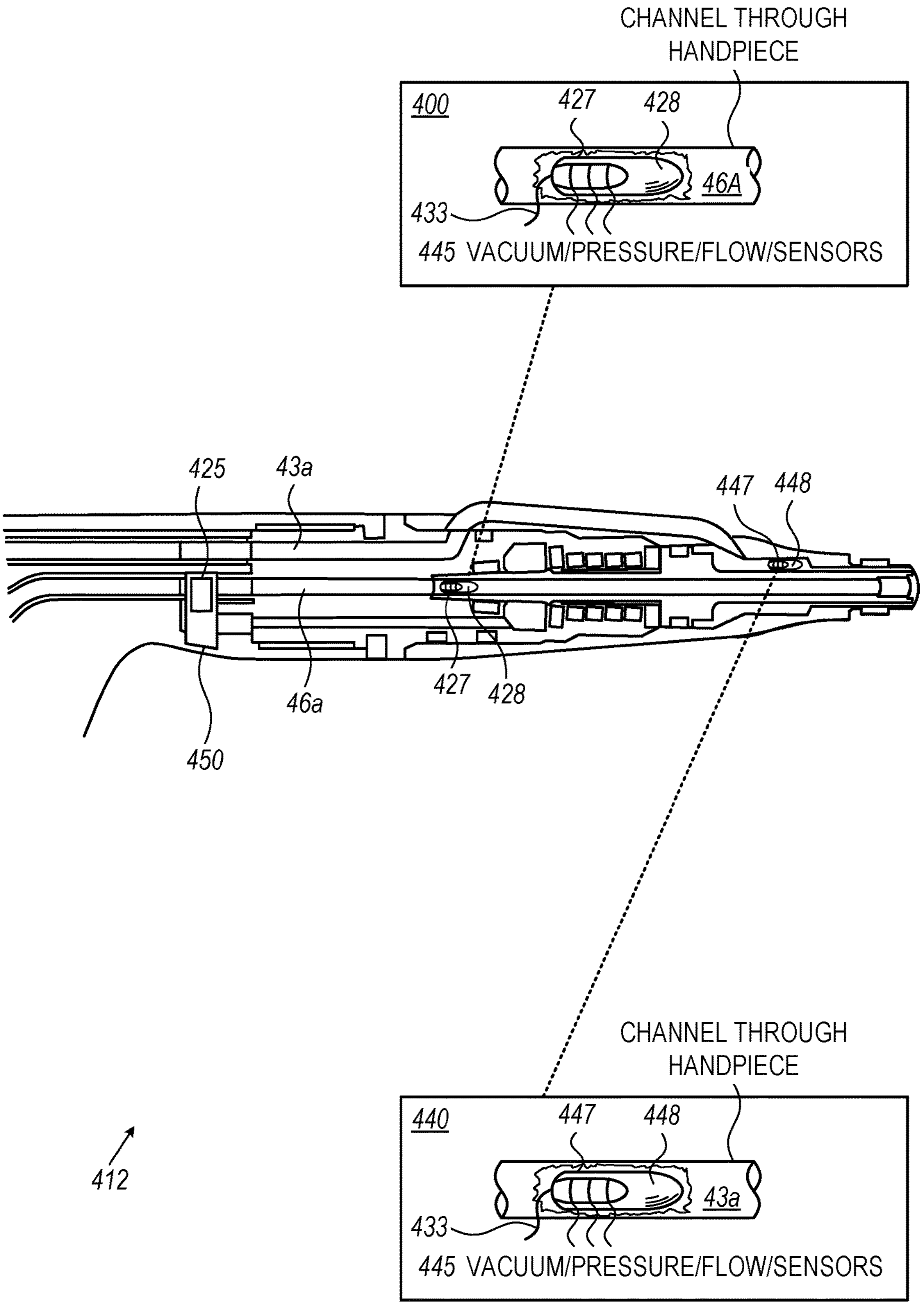
FIG. 4 is a schematic, orthographic side view of a phacoemulsification handpiece including two sensing arrays, one put at a distal location on an aspiration channel and the other on an irrigation channel, in accordance with some examples of the present disclosure.

The sensor arrays are embedded into a handpiece of a phacoemulsification probe. The disclosed solutions take advantage of the available space along the rigid flow channels to include multiple vacuum/pressure/flow sensors. In one example, a blind hole may be formed in the rigid channel and the sensor array may be mounted in the blind hole so that it may sense the pressure without obstructing the flow. Such example is shown in FIG. 4.

Figure 2:
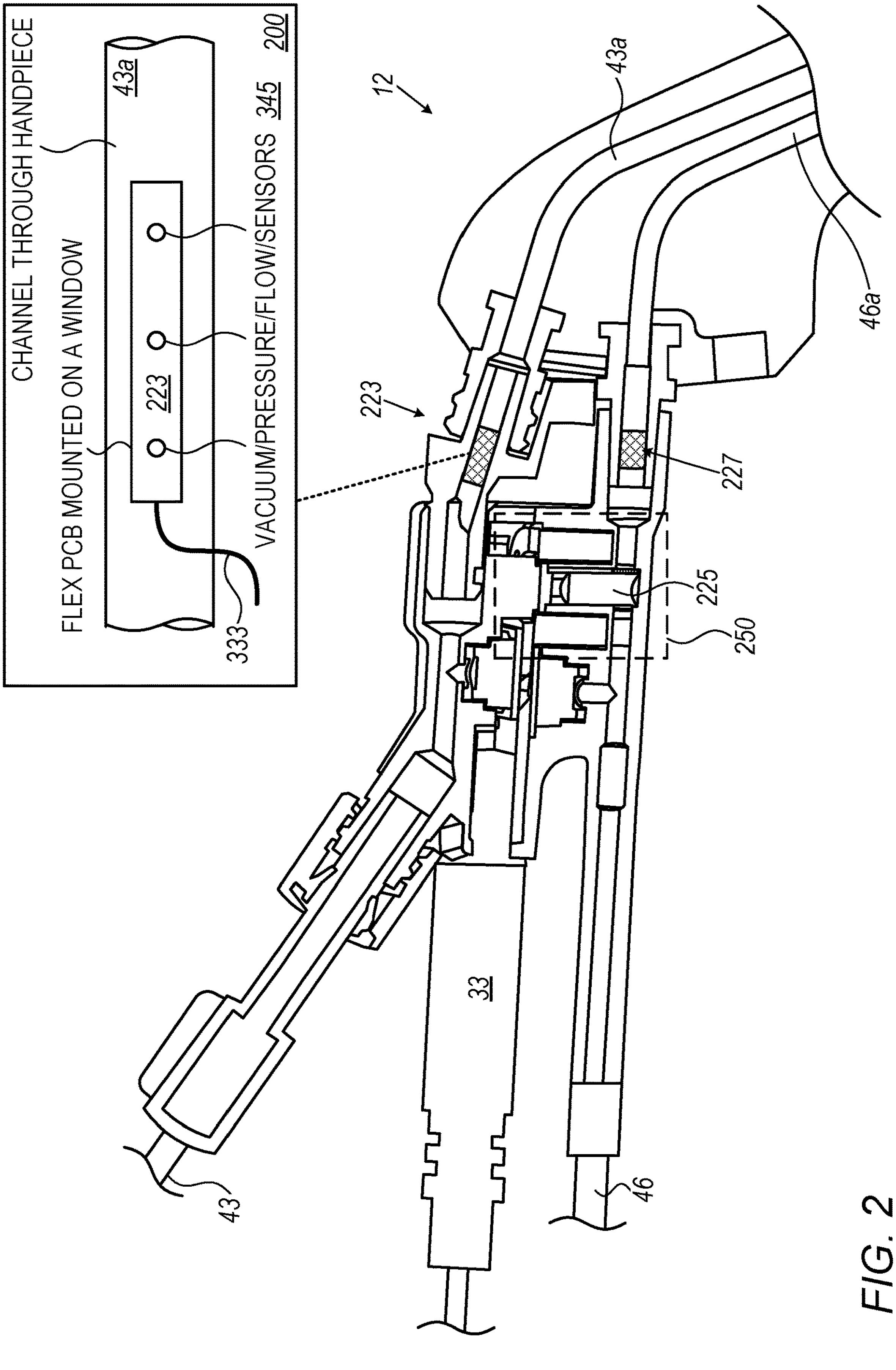
FIG. 2 is a schematic, orthographic side view of a phacoemulsification handpiece including sensing arrays on aspiration and irrigation channels inside the handpiece, in accordance with an example of the present disclosure.

In another example, each group of sensors may be mounted on a flexible Printed circuit Board (PCB) that is embedded within a rigid flow channel of the handpiece. The sensors that form a sensor array are fluidly coupled to the port made. In another example, a window may be formed in the rigid channels and the flex PCB may be mounted and sealed on the window. This example is shown in FIG. 2. The different sensor arrays may be suitable for undergoing sterilization.

In one example, readings are taken from all of the pressure sensors of a given sensor array and the readings are compared. It is expected that all of the readings on a same channel will provide substantially the same output. Significant differences may indicate that there is some malfunction that should be checked. A warning provided to the user to check the integrity of the device will be included.

Furthermore, in some embodiments each sensor array comprises an odd number of sensors, which can overcome malfunction of an individual sensor by enabling a majority decision. Thus, even if a single sensor provides an outlier reading, the clinical procedure can be completed without hazard.

System Description

Figure 1:
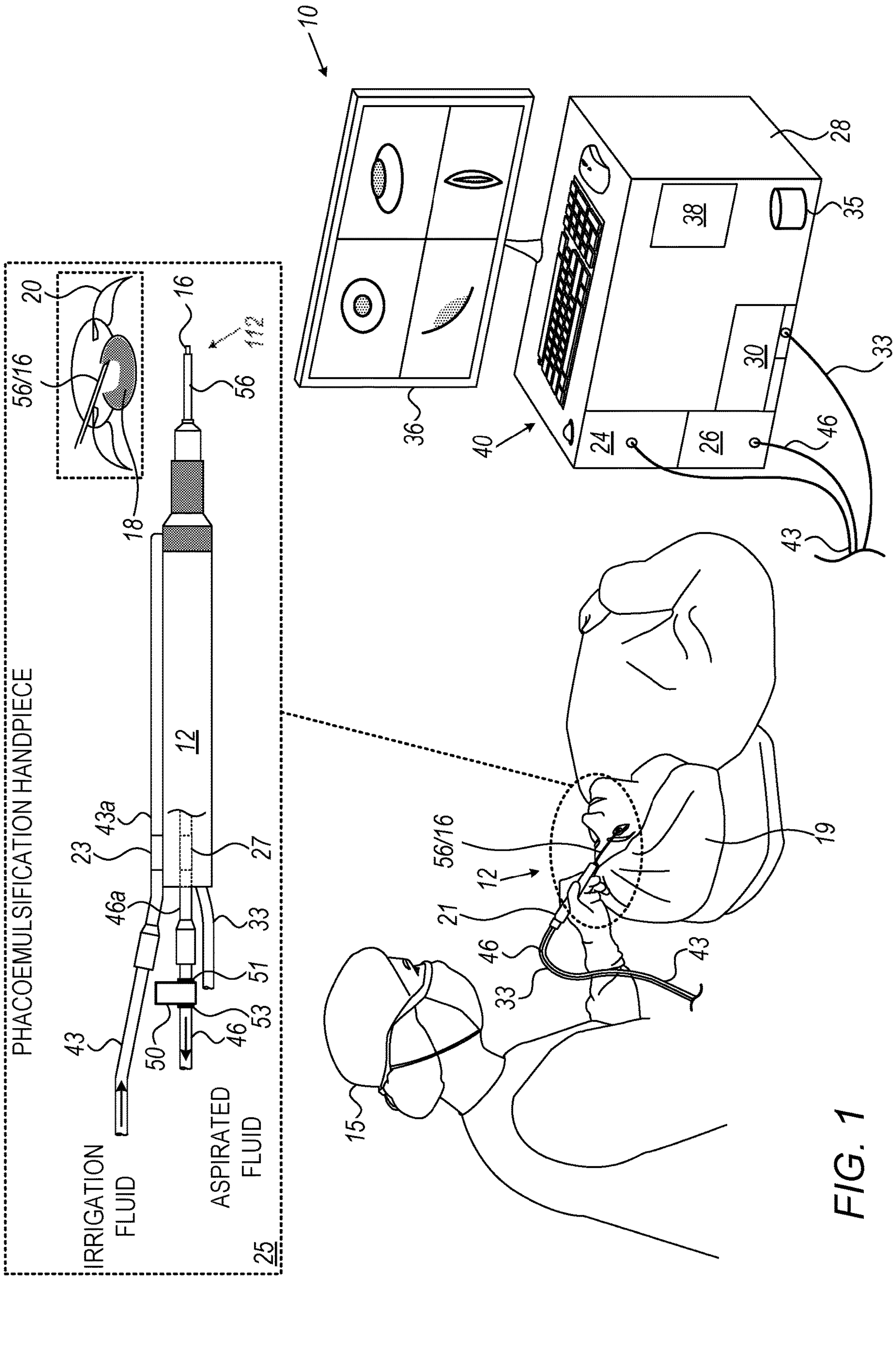
FIG. 1 is a schematic, pictorial view, along with an orthographic side view, of a phacoemulsification system comprising a phacoemulsification handpiece fitted with aspiration and irrigation sensor arrays, in accordance with an example of the present disclosure.

FIG. 1 is a schematic, pictorial view, along with an orthographic side view, of a phacoemulsification system 10 comprising a phacoemulsification handpiece fitted with aspiration and irrigation sensor arrays 27 and 23, respectively, in accordance with an example of the present disclosure.

As seen in the pictorial view of phacoemulsification system 10, and in inset 25, a phacoemulsification probe 12 (e.g., a handpiece) comprises a needle 16 and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, the irrigation sleeve may have one or more side ports at or near the distal end to allow irrigation fluid to flow toward the distal end of the handpiece through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Irvine, CA, USA.

In the shown example, during the phacoemulsification procedure a pumping subsystem 24 comprised in a console 28 pumps irrigation fluid from an irrigation reservoir (not shown) to the irrigation sleeve 56 to irrigate the eye. The fluid is pumped via an irrigation tubing line 43 running from the console 28 to an irrigation channel 43*a* of probe 12. Eye fluid and waste matter (e.g., emulsified parts of the cataract) are aspirated via hollow needle 16 to a collection receptacle (not shown) by a pumping subsystem 26, also comprised in console 28, using an aspiration tubing line 46 running from aspiration channel 46*a* of probe 12 to console 28. In another example, the pumping subsystem 24 may be coupled or replaced with a gravity-fed irrigation source such as a balanced salt solution bottle/bag.

System 10 includes standalone disposable detachable add-on module 50, coupled via fluid connectors 51 and 53, to control (e.g., regulate) aspiration flow rate to reduce risks to eye 20 from irregular performance of aspiration in probe 12, such as from a vacuum surge.

An example of module 50 is an anti-vacuum surge (AVS) device, which is described in U.S. patent application Ser. No. 17/130,409, filed on Dec. 22, 2020, and titled, "A module for Aspiration and Irrigation Control," which is assigned to the assignee of the present application.

Module 50 can discontinue aspiration in order to provide a fast response (e.g., within several milliseconds) to a detected vacuum surge. Module 50 has its own processor and can be used with existing phacoemulsification systems as a disposable element that improves control over intraocular pressure (IOP) during a surgical cataract removal procedure.

In the shown example, fast and robust IOP control (e.g., by module 50) is facilitated by module 50 receiving real-time readings from sensor arrays 23 and 27. Sensor array 23 comprises an odd number of pressure sensors (e.g., three) that are fluidly coupled to irrigation channel 43*a*. Sensor array 27 comprises an odd number of vacuum sensors (e.g., three or five) that are fluidly coupled to aspiration channel 46*a*. An example of such a sensor array is described in detail in FIG. 2.

Phacoemulsification probe 12 includes other elements (not shown), such as one or more piezoelectric crystals coupled with a horn to drive vibration of needle 16. The piezoelectric crystal is configured to vibrate needle 16 in a resonant vibration mode. The vibration of needle 16 is used to break a cataract into small pieces during a phacoemulsification procedure. Console 28 comprises a piezoelectric drive module 30, coupled with the piezoelectric crystal, using electrical wiring running in a cable 33. Drive module 30 is controlled by a processor 38 and conveys processor-controlled driving signals via cable 33 to, for example, maintain needle 16 at selected vibration amplitude. The drive module may be realized in hardware or software, for example, in a proportional-integral-derivative (PID) control architecture.

Processor 38 may receive user-based commands via a user interface 40, which may include setting a vibration mode, duty cycle, and/or frequency of the piezoelectric crystal, and setting or adjusting an irrigation and/or aspiration rate of the pumping subsystems 24/26. In an example, user interface 40 and display 36 may be combined as a single touch screen graphical user interface. In an example, the physician uses a foot pedal (not shown) as a means of control and an encoder sensing position of the foot pedal may provide input to processor 38. Additionally or alternatively, processor 38 may receive the user-based commands from controls located in a handle 21 of probe 12.

Some or all of the functions of processor 38 may be combined in a single physical component or, alternatively, implemented using multiple physical components. These physical components may comprise hard-wired or programmable devices, or a combination of the two. In some examples, at least some of the functions of processor 38 may be carried out by suitable software stored in a memory 35 (as shown in FIG. 1). This software may be downloaded to a device in electronic form, over a network, for example. Alternatively or additionally, the software may be stored in tangible, non-transitory computer-readable storage media, such as optical, magnetic, or electronic memory.

The apparatus shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

In some examples, a different type of AVS module can be used that is coupled only with the aspiration part of the system (i.e., without involving irrigation).

Sensor Arrays Incorporation and Functionality

FIG. 2 is a schematic, orthographic side view of a phacoemulsification handpiece 12 including sensing arrays 227 and 223 on respective aspiration and irrigation channels 46*a* and 43*a* inside the handpiece, in accordance with an example of the present disclosure. FIG. 2 further shows a standalone disposable detachable aspiration control module 250, coupled to control aspiration flow rates to reduce risks to eye 20 from irregular performance of aspiration and/or irrigation in probe 12, such as from a vacuum surge.

Module 50 is an example of the aforementioned anti-vacuum surge (AVS) device, where, in the example shown in FIG. 2, a protection valve 225 of module 250 can regulate aspiration flow based on vacuum readings from sensor array 227.

Optionally, module 250 can be replaced with an alternate module that includes a diversion valve (i.e., a bypass valve) configured to divert irrigation flow into the aspiration channel based on processor commands according to pressure readings from sensor array 223 and/or vacuum readings from sensor array 227.

Inset 200 provides a detailed view of pressure sensor array 223. As seen, the array is made of an odd number of sensors 345. During priming, if readings from all sensors 345 provide same output this is an indication that the pressure sensors are operating correctly. If not, then apparently there has been some damage and the handpiece is faulty. The array 223 is realized on a flexible PCB substrate that is attached (e.g., glued) to rigid channel 43*a*.

Sensors 345 are fluidly coupled to channel 43*a* via one or more windows formed in the rigid channels with the flex PCB substrate of array 223 sealed against the one or more windows. A multiwire electrical cable 333 connects the sensors (e.g., via cable 33) via an interface to a processor.

The handpiece shown in FIG. 2 is simplified for clarity. It may include further elements which are omitted for simplicity of presentation, such as an inset detailing sensor array 227, which will be similar to inset 200 detailing array 223.

Figure 3:
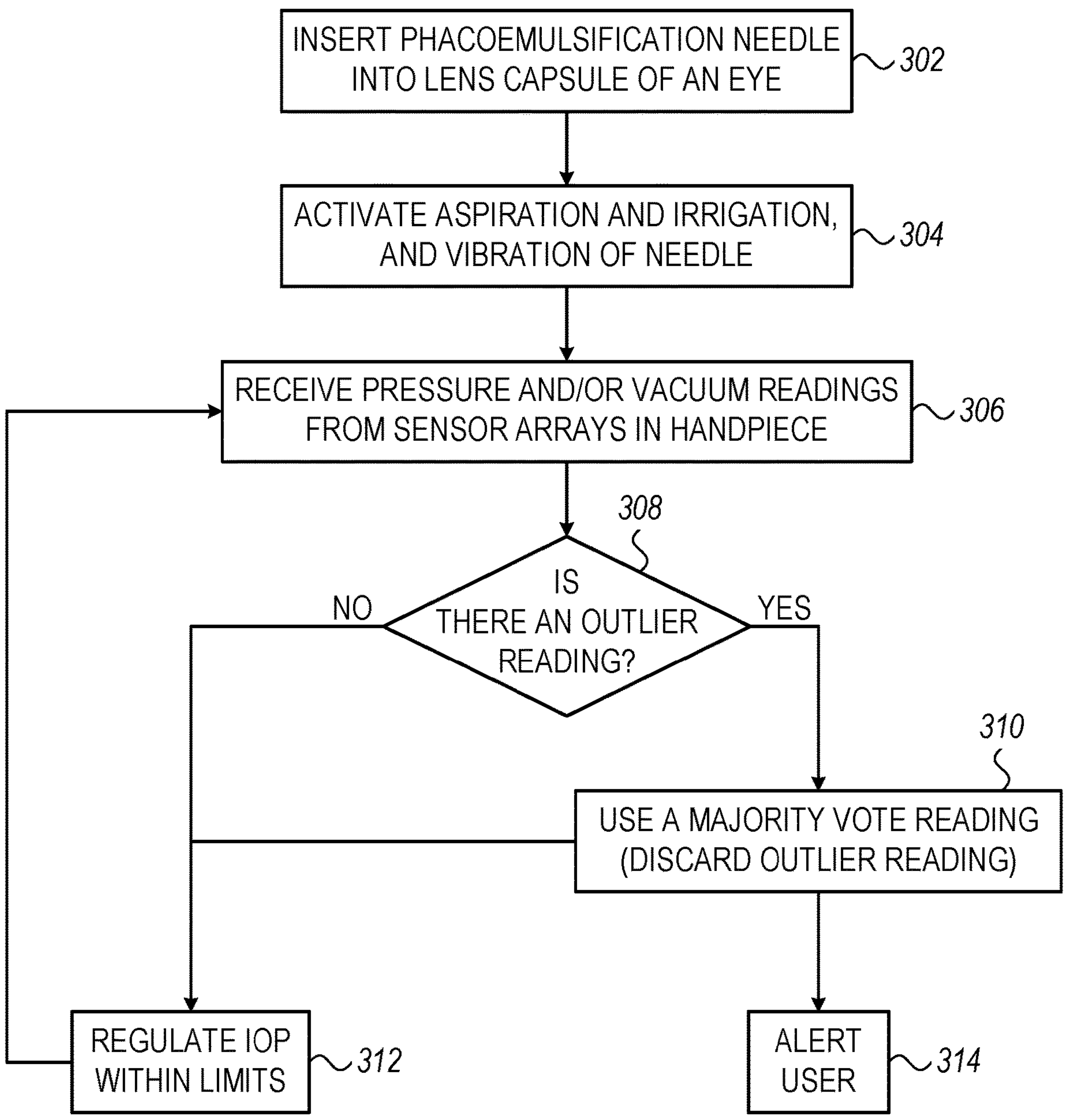
FIG. 3 is a flow chart schematically illustrating a method for measuring aspiration and irrigation parameters using the sensing arrays of FIG. 2, in accordance with some examples of the present disclosure.

Method of Majority Decision Using Sensor Array Inside a Phacoemulsification Handpiece FIG. 3 is a flow chart schematically illustrating a method for measuring aspiration and irrigation parameters using the sensing arrays 223 and 227 of FIG. 2, in accordance with some examples of the present disclosure. The process begins with physician 15 inserting phacoemulsification needle 16 of probe 12 into a lens capsule 18 of an eye 20, at a phacoemulsification needle insertion step 302.

At a phacoemulsification step 304, physician 15 presses a foot pedal to a first position to activate aspiration, subsequently to a second position to activate irrigation, and finally, when the foot pedal is pressed and placed in a third position, the needle 16 is vibrated to perform the phacoemulsification.

During phacoemulsification, processor 38 receives pressure and vacuum readings from sensor arrays 223 and 227, respectively, at readings receiving step 306.

At a checking step 308, the processor checks if there is an outlier reading among the sensors. If the answer is no the process proceeds directly to IOP regulation step 312.

If the answer is yes, the processor uses a majority vote reading (i.e., discards an outlier reading), at a majority readings step 310.

At IOP regulation step 312, the processor uses accepted sensor array readings to maintain IOP within specified limits.

If required, at an alerting step 314, the processor alerts physician 15 of a possible malfunction of a sensor in the handpiece.

Distally Located Sensor Arrays in Aspiration Channel

FIG. 4 is a schematic, orthographic side view of a phacoemulsification handpiece 412 including two sensing arrays 427 and 447, one (427) put at a distal location on an aspiration channel 46*a* and the other (447) on an irrigation channel 43*a*, in accordance with some examples of the present disclosure.

FIG. 4 further shows a standalone disposable detachable aspiration control module 450 comprising a protection valve 225, coupled to control aspiration flow rates to reduce risks to an eye from irregular performance of aspiration in the handpieces, such as from a vacuum surge.

Inset 400 provides a detailed view of pressure sensor array 427. As seen, the array is made of an odd number of sensors 445. During priming, a processor checks the integrity of sensors 445 by comparing output readings from all of them. If they all have the same output readings, up to a tolerance, the processor determines that the pressure sensors are working well. Furthermore, during the surgical procedure, in case of a malfunctioning sensor, a majority decision can still be made based on the array readings.

The array is put inside an indentation 428 that is made into the inner wall of the rigid channel 46*a*, e.g., using blind drilling. Using the indentation ensures flow in the rigid channel is not disturbed by the sensors.

Further seen is a multiwire electrical cable 433 may extend through the aspiration channel or may extend outside of the channel through a dedicated port penetration through the channel.

Inset 440 provides a detailed view of pressure sensor array 447. Again, the array is made of the odd number of sensors 445, so that, during priming, the processor checks the integrity of sensors 445 by comparing output readings from all of them.

The array 447 is also put inside an indentation 448 that is made into the inner wall of the rigid channel 43*a*, e.g., using blind drilling. Using the indentation ensures flow in the rigid channel is not disturbed by the sensors.

Testing Sensor Arrays During Priming

As noted above, testing the sensor arrays before each procedure can indicates malfunction of individual sensors.

Figure 5:
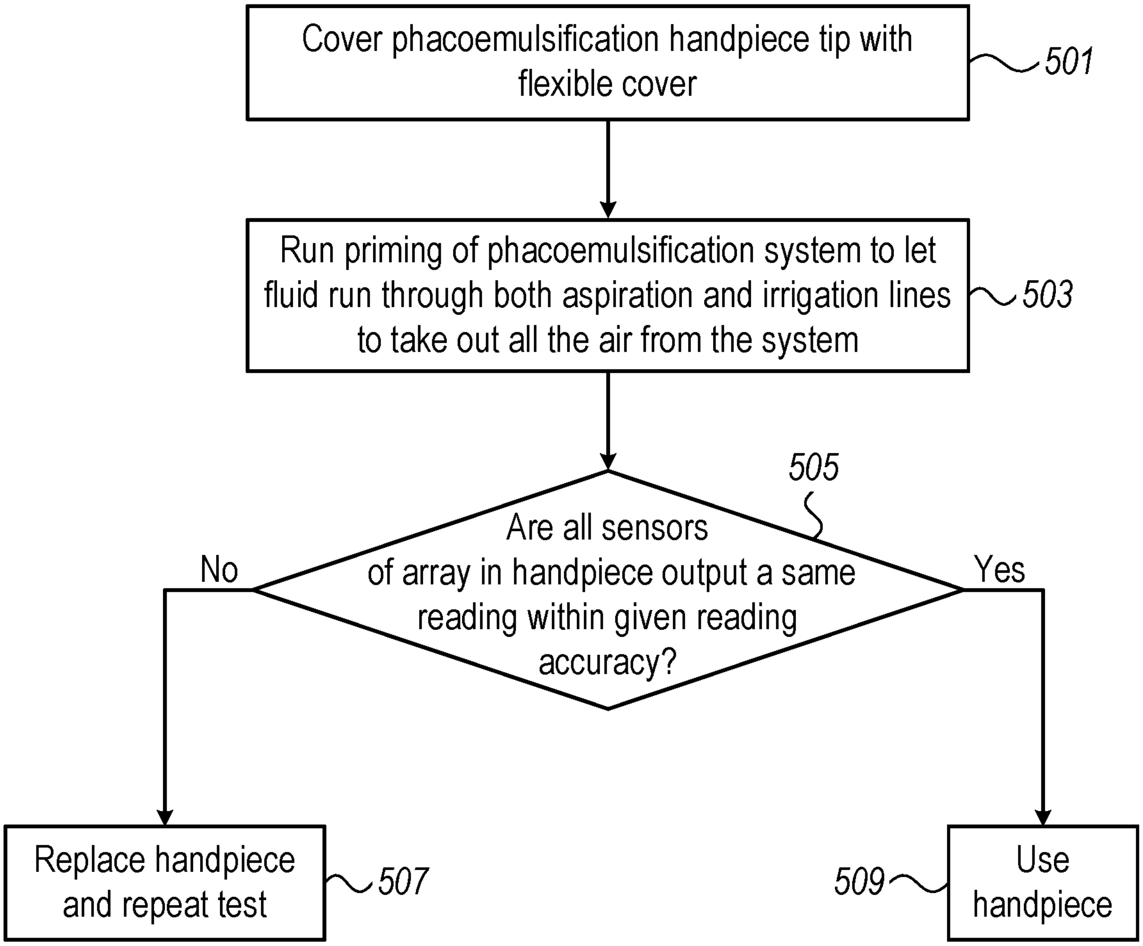
FIG. 5 is a flow chart schematically illustrating a method for testing the sensor arrays of FIG. 4 during priming, in accordance with some examples of the present disclosure.

FIG. 5 is a flow chart schematically illustrating a method for testing the sensor arrays of FIG. 4 during priming, in accordance with some examples of the present disclosure. The process begins at a tip covering step 501, with physician 15 covering the phacoemulsification handpiece tip with a flexible cover to generate a place holder for irrigation fluid.

Next, at a priming step 503, physician 15 starts priming of system 10 to let fluid fill the aspiration and irrigation lines, at a system priming step 503. During priming the physician keeps the handpiece tip immersed in irrigation fluid accumulated inside the flexible cover.

At sensor array checking step 505, the processor checks if the output (e.g., readings) from each of the sensors 445 is substantially the same. If the answer is no, the physician replaces the handpiece and repeats the test with a new handpiece, at a new test during priming step 507. If the answer is yes, the physician can use the handpiece, at a handpiece readiness granting step 509.

EXAMPLES

Example 1

A phacoemulsification system (10) includes a phacoemulsification probe (12) and a processor (38). The phacoemulsification probe has a distal end (112) configured for insertion into an eye of a patient, the probe including (i) an irrigation channel (43*a*) for irrigating the eye with irrigation fluid, (ii) an aspiration channel (46*a*) for evacuating material from the eye, and (iii) at least one sensor array (223, 227,

427, 447) fluidly coupled to at least one of the irrigation channel and the aspiration channel, the at least one sensor array comprising multiple sensors (345, 445) configured to measure a parameter indicative of fluid pressure in the irrigation channel or the aspiration channel. The processor (38) is configured to regulate at least one of irrigation flow and aspiration flow using the measured parameter.

Example 2

The system (10) according to example 1, wherein the processor (38) is configured to alert a user in case of at least one of the sensors (345, 445) of the at least one of the sensor arrays (223, 227, 427, 447) malfunctioning.

Example 3

The system (10) according to any of examples 1 and 2, wherein the sensor array (227, 447) is coupled with the irrigation channel (43*a*), and wherein the sensors (345, 445) are configured to measure a pressure of the irrigation fluid.

Example 4

The system (10) according to any of examples 1 through 3, wherein the sensor array (447) is fitted into an indentation made (448) in an inner wall of the irrigation channel (43*a*).

Example 5

The system (10) according to any of examples 1 through 4, wherein the sensor array (223, 427) is coupled with the aspiration channel (46*a*), and wherein the sensors (345, 445) are configured to measure a vacuum level in the aspiration channel (46*a*).

Example 6

The system (10) according to any of examples 1 through 5, wherein the sensor array (427) is fitted into an indentation (428) made in an inner wall of the aspiration channel (46*a*).

Example 7

The system (10) according to any of examples 1 through 6, wherein the at least one sensor array (223, 227, 427, 447) comprises an odd number of the sensors (345, 445), and wherein the processor (38) is configured to perform a majority vote among readings of the sensors (345, 445) of the array (223, 227, 427, 447).

Example 8

The system (10) according to any of examples 1 through 7, wherein the at least one sensor array (223, 227, 427, 447) is comprised in a handpiece of the phacoemulsification probe (12) and is suitable for undergoing sterilization.

Example 9

The system (10) according to any of examples 1 through 8, wherein the sensor array (223, 227) is disposed on a flexible PCB.

Example 10

The system (10) according to any of examples 1 through 9, wherein the irrigation channel (43*a*) or the aspiration channel (46*a*) comprises a window formed therein, and wherein the flexible PCB is coupled with the window.

Example 11

A phacoemulsification method includes inserting into an eye (20) of a patient a distal end (112) of a phacoemulsification probe (12), the probe including (i) an irrigation channel (43*a*) for irrigating the eye with irrigation fluid, (ii) an aspiration channel (46*a*) for evacuating material from the eye, and (iii) at least one sensor array (223, 227, 427, 447) fluidly coupled to at least one of the irrigation channel and the aspiration channel, the at least one sensor array comprising multiple sensors (345, 445) configured to measure a parameter indicative of fluid pressure in the irrigation channel or the aspiration channel. At least one of irrigation flow and aspiration flow are regulated using the measured parameter.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification system, comprising:

a phacoemulsification probe having a distal end configured for insertion into an eye of a patient, the probe comprising:

an irrigation channel for irrigating the eye with irrigation fluid;

an aspiration channel for evacuating material from the eye; and at least one sensor array fluidly coupled to at least one of the irrigation channel and the aspiration channel, the at least one sensor array comprising multiple sensors configured to measure a parameter indicative of fluid pressure in the irrigation channel or the aspiration channel; and a processor, which is configured to regulate at least one of irrigation flow and aspiration flow using the measured parameter, wherein the at least one sensor array comprises an odd number of the sensors, and wherein the processor is configured to perform a majority vote among readings of the sensors of the array.

2. The system according to claim 1, wherein the processor is configured to alert a user on a condition of at least one of the sensors of the at least one of the sensor arrays malfunctioning.

3. The system according to claim 1, wherein the sensor array is coupled with the irrigation channel, and wherein the sensors are configured to measure a pressure of the irrigation fluid.

4. The system according to claim 3, wherein the sensor array is fitted into an indentation made in an inner wall of the irrigation channel.

5. The system according to claim 1, wherein the sensor array is coupled with the aspiration channel, and wherein the sensors are configured to measure a vacuum level in the aspiration channel.

6. The system according to claim 5, wherein the sensor array is fitted into an indentation made in an inner wall of the aspiration channel.

7. The system according to claim 1, wherein the at least one sensor array is comprised in a handpiece of the phacoemulsification probe and is suitable for undergoing sterilization.

8. A phacoemulsification system, comprising:

a phacoemulsification probe having a distal end configured for insertion into an eye of a patient, the probe comprising:

an irrigation channel for irrigating the eye with irrigation fluid;

an aspiration channel for evacuating material from the eye; and at least one sensor array fluidly coupled to at least one of the irrigation channel and the aspiration channel, the at least one sensor array comprising multiple sensors configured to measure a parameter indicative of fluid pressure in the irrigation channel or the aspiration channel; and a processor, which is configured to regulate at least one of irrigation flow and aspiration flow using the measured parameter, wherein the sensor array is disposed on a flexible printed circuit board (PCB).

9. The system according to claim 8, wherein the irrigation channel or the aspiration channel comprises a window formed therein, and wherein the flexible PCB is coupled with the window.

* * * * *